United States Patent
Alqam et al.

(10) Patent No.: US 11,733,136 B2
(45) Date of Patent: Aug. 22, 2023

(54) FLUID SENSITIVITY EVALUATION METHOD FOR SUPERIOR WATER-BASED MUD DESIGN

(71) Applicant: SAUDI ARABIAN OIL COMPANY, Dhahran (SA)

(72) Inventors: Mohammad H. Alqam, Dhahran (SA); Md Amanullah, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 69 days.

(21) Appl. No.: 17/643,663

(22) Filed: Dec. 10, 2021

(65) Prior Publication Data

US 2023/0184646 A1 Jun. 15, 2023

(51) Int. Cl.
*G01N 3/08* (2006.01)
*G01N 1/28* (2006.01)
*G01N 33/24* (2006.01)

(52) U.S. Cl.
CPC ............. *G01N 3/08* (2013.01); *G01N 1/28* (2013.01); *G01N 33/24* (2013.01); *G01N 2203/0019* (2013.01); *G01N 2203/0067* (2013.01)

(58) Field of Classification Search
CPC .. G01N 1/28; G01N 33/24; G01N 2203/0019; G01N 2203/0067; G01N 3/08
USPC .......................................................... 73/821
See application file for complete search history.

(56) References Cited

U.S. PATENT DOCUMENTS

| | | | |
|---|---|---|---|
| 3,680,963 A | | 8/1972 | Edwards et al. |
| 5,416,697 A | * | 5/1995 | Goodman ............. E21B 49/006 702/9 |
| 8,186,875 B2 | | 5/2012 | Tognarelli et al. |
| 8,379,483 B2 | | 2/2013 | Tang et al. |

(Continued)

FOREIGN PATENT DOCUMENTS

| | | |
|---|---|---|
| CA | 2558627 C | 11/2009 |
| CN | 105067794 A | 11/2015 |

(Continued)

OTHER PUBLICATIONS

Al-Bazali, "The impact of water content and ionic diffusion on the uniaxial compressive strength of shale", Egyptian Journal of Petroleum (2013) 22, 249-260 (Year: 2013).*

(Continued)

*Primary Examiner* — Nathaniel T Woodward
(74) *Attorney, Agent, or Firm* — Osha Bergman Watanabe & Burton LLP

(57) ABSTRACT

A method of evaluating fluid sensitivity of a water-based muds on a shale rock. The method includes providing a sample of the shale rock from a portion of a formation, where the portion of the formation is positioned outside of a reservoir region. The sample of the shale rock is separated into a first portion and a second portion. The first portion is subjected to a UCS test for detecting a first uniaxial compressive strength (UCS) value ($UCS_o$). The second portion is converted into a prepared sample utilizing a test preparation procedure. The prepared sample is subjected to the UCS test for detecting a second UCS value ($UCS_1$). A fluid sensitivity index (FSI) is determined utilizing the detected $UCS_0$ and $USC_1$ values.

8 Claims, 3 Drawing Sheets

(56) References Cited

U.S. PATENT DOCUMENTS

| | | |
|---|---|---|
| 9,771,795 B2 | 9/2017 | Knight et al. |
| 10,267,136 B2 | 4/2019 | Huang et al. |
| 2010/0212892 A1 | 8/2010 | Santra et al. |

FOREIGN PATENT DOCUMENTS

| | | |
|---|---|---|
| CN | 105370267 A | 3/2016 |
| CN | 107884261 A | 4/2018 |
| CN | 111738616 A | 10/2020 |
| CN | 108071389 B | 3/2021 |
| KR | 101716492 B1 | 3/2017 |
| WO | 2021077938 A1 | 4/2021 |

OTHER PUBLICATIONS

Mohamed et al., "Uniaxial Compressive Strength of Composite Rock Material with respect to Shale Thickness Ratio and Moisture Content", EJGE, vol. 13, Bund. A, p. 1-10 (Year: 2007).*

Farrokhrouz, Mohsen, et al., "Empirical estimation of uniaxial compressive strength of shale formations", Geophysics, Society of Exploration Geophysicists, vol. 79, No. 4, Jul.-Aug. 2014, pp. 1-8 (9 pages).

\* cited by examiner

FLUID SENSITIVITY EVALUATION METHOD FOR SUPERIOR WATER-BASED MUD DESIGN

BACKGROUND

As wellbores are drilled, the composition and properties of the rocks the drill encounters may change as depth increases. Certain types of rocks may react differently with various drilling fluids, causing instability of the wellbore at different depths. Oil-based muds are known to be highly unreactive but are disfavored due to their effects on the surrounding environment. Water-based muds are reactive to the wellbore rock surface but have less of a detrimental effect to the surround environment.

Accordingly, the mechanical properties of sub surface rocks are important for geo-mechanical modelling and mechanical stabilization of near wellbore formations for safe and trouble-free drilling operations. Typically, the original rock physio-mechanical properties, such as the uniaxial compressive strength, Young's modulus, and Poisson's ratios, are used for modelling and prediction of mechanical stability of near wellbore formations without considering the geo-mechanical effect of rock-fluid interactions.

Experience shows that the presence of a sensitive fluid to the wellbore environment, such as non-inhibitive or low-inhibitive water-based muds, can cause serious damage and degradation of the mechanical properties of the rock leading to a drastic reduction of the virgin rock mechanical properties. As such, the use of the virgin rock mechanical properties in geo-mechanical modelling may lead to misleading information while drilling. Thus, the need for an assessment of the sensitivity of a drilling mud on the rock formation is necessary to provide accurate and reliable input data for geo-mechanical modelling.

SUMMARY

This Summary is provided to introduce a selection of concepts that are further described in the Detailed Description. This Summary is not intended to identify key or essential features of the claimed subject matter, nor is it intended to be used as an aid in limiting the scope of the claimed subject matter.

In one aspect, embodiments disclosed relate to a method of evaluating fluid sensitivity of a water-based muds on a shale rock. The method includes providing a sample of the shale rock from a portion of a formation, where the portion of the formation is positioned outside of a reservoir region. The sample of the shale rock is separated into a first portion and a second portion. The first portion is subjected to a UCS test for detecting a first uniaxial compressive strength (UCS) value ($UCS_o$). The second portion is converted into a prepared sample utilizing a test preparation procedure. The prepared sample is subjected to the UCS test for detecting a second UCS value ($UCS_1$). A fluid sensitivity index (FSI) is determined utilizing the detected $UCS_0$ and $USC_1$ values Other aspects and advantages of the claimed subject matter will be apparent from the following description and the appended claims.

DETAILED DESCRIPTION

Figure 1:
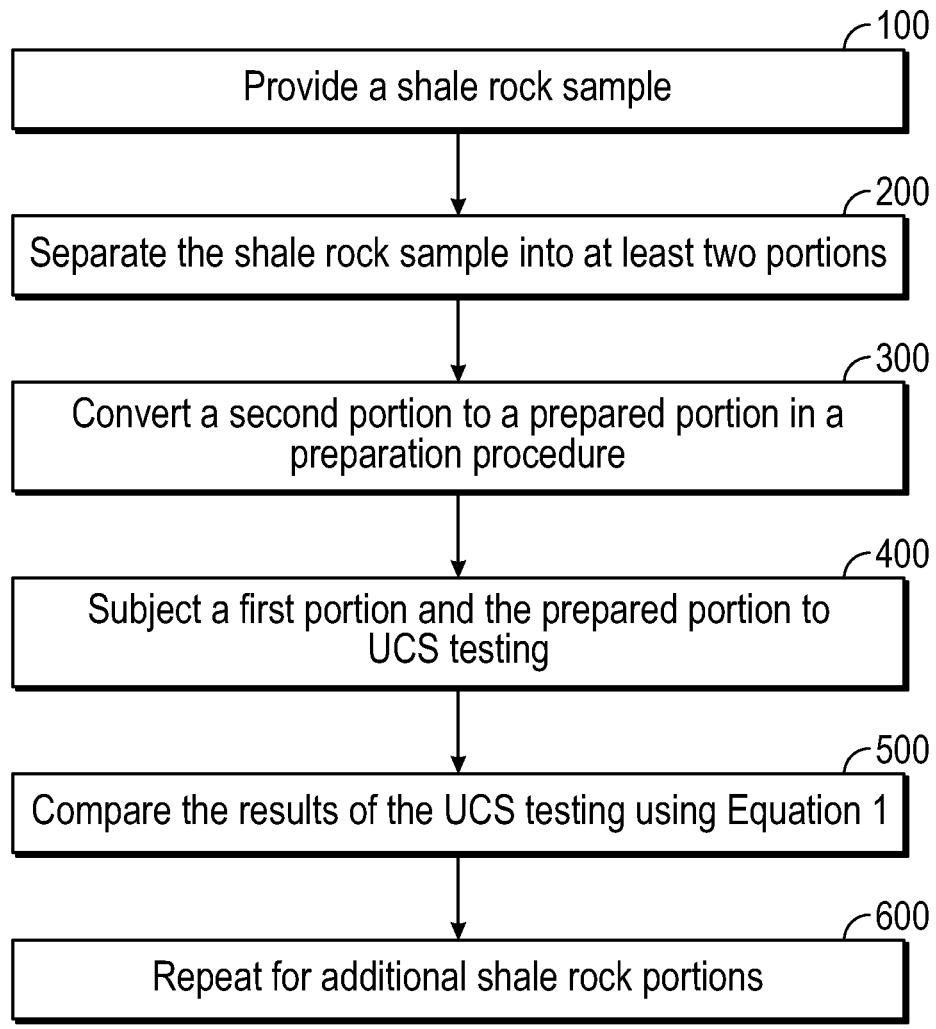
FIG. 1 is a simplified block flow diagram of a testing procedure according to one or more embodiments disclosed.

For the purpose of this description, a single reference number will be assigned to a line as well as a stream carried in that line. Same reference numbers refer to similar components. The person skilled in the art will readily understand that, while the invention is illustrated referring to one or more specific combinations of features and measures, many of those features and measures are functionally independent from other features and measures such that they can be equally or similarly applied independently in other embodiments or combinations.

One or more embodiments disclosed is an American Petroleum Institute (API) method for determining a dimensionless Fluid Sensitivity Index (FSI) based on geo-mechanical degradation for use in various water-based drilling mud systems. The method may be reliable, repeatable, and easily executable for mechanical assessment of rock-fluid interaction.

The FSI is defined as the fractional loss of uniaxial compressive strength (UCS) value of reactive shale or mudrock with respect to the original UCS value ($UCS_o$) of the sample before interaction with a fluid system and $USC_1$ is the UCS value of a rock sample that has undergone a preparation procedure. Mathematically, it can be expressed by Equation (1):

$$FSI = \frac{\Delta UCS}{UCS_o} \quad \text{(Eq. 1)}$$

where $\Delta UCS$ is the difference between $UCS_o$ and $UCS_1$.

Mud systems that cause no damage or degradation of shale and mudrock will have a FSI value equal to zero (0) as the $USC_o$ and $USC_1$ will be the same. This indicates an insensitive (non-reactive) mud system, which may be considered the most desirable drilling mud for trouble free drilling operation in regard to interaction with the formation material. On the other hand, mud systems that cause total degradation of the shale rock will have a FSI value equal to one (1), which may be considered the least desirable drilling mud for trouble free drilling operations in regard to the interaction with the formation material. Due to the nature of the drilling fluids, all inhibitive mud systems will have FSI values between the two extremes. Greater inhibition potential of the drilling mud systems results in a reduced FSI value.

As part of the method, a uniaxial compressive strength (UCS) test is performed on various rock samples using various water-based muds. The UCS test is a laboratory test used to derive the UCS of a rock sample. The UCS indicates the maximum axial compressive stress that a sample can bear under zero confining stress. That is, pressure or force is only applied to a single axis of the sample, such as the longitudinal axis.

Samples are retrieved by drill cores and are selected in order to be representative of the original rock formation. The ratio of the major axis (longitudinal) length of the sample to diameter of the sample (L/D) may be between 2.0 and 5.0. The cylindrical surfaces are cored in such a way that they are provided to be flat and smooth. In this fashion, the terminal ends of the sample may be approximately level.

The apparatus used to conduct the UCS test has a loading device, two parallel plates, and a strain measurement device or force gauge. The loading device allows for a consistently applied load at the required load rate until the end of the test. The longitudinal stress applied by the loading device is transferred to the specimen by two parallel plate that are made with a hardened material. The diameter of the plates is at least equal to the diameter of the sample. The axial and lateral deformations are measured by various devices known in the art, such as linear variable differential transformers (LVDTs), electrical resistance strain gauges, other such devices that measure force.

During UCS testing, the load may be continuously applied by the loading device and two parallel plates at a rate of 0.1 megapascal per second (MPa/s) to 2.0 MPa/s. Stress and deformation data may be recorded through an electronic system that has the appropriate accuracy necessary for the test. The UCS is the peak value (in MPa) when the sample fails or breaks apart. During the failure process, cracks normally propagate along the length of the sample in the direction the force is applied.

Turning now to the Figures, according to FIG. 1 a testing methodology for evaluating fluid sensitivity of a water-based muds on a shale rock according to one or more embodiments is described. A shale rock sample is provided in step 100. The shale rock sample may be provided from an upper portion of the formation. This portion of the formation may be above the region where water, hydrocarbons, or other reservoir fluids may be located. Accordingly, the upper region may be primarily a zone where non-reservoir shale rock is located.

The shale rock sample provided in step 100 may be separated into multiple portions in step 200. For example, the shale rock sample may be separated by known cleaving methods into a first portion, a second portion, a third portion, a fourth portion, and so forth.

The first portion of the shale rock sample may act as a control sample for the purposes of UCS testing. The control sample represents unaltered, virgin rock material. The first sample may be subjected to UCS testing in an unaltered state in step 400. The UCS test of the first portion may provide a base UCS value ($UCS_o$).

The second portion of the shale rock sample may be subjected to a preparation procedure in step 300. The preparation procedure may subject the second portion of the rock sample to a water-based mud or water-based mud analog. This may deteriorate, damage, or otherwise weaken the rock sample such that the rock sample has the same physio-mechanical properties as the rock in the formation along the wellbore wall after drilling operations with the same, or similar, water-based muds.

The rock samples, after being subjecting to the preparation procedure in step 300, may also be subjected to the UCS testing in step 400, under the same conditions as the first portion of the rock sample. The UCS testing of the rock samples that were subjected to the preparation procedure may produce a first UCS value ($UCS_1$), a second UCS value ($UCS_2$), a third UCS value ($UCS_3$), and so forth.

After the UCS testing has been completed on the first and second portions of the rock sample, the results may be compared in step 500 using Equation 1.

Steps 300, 400, and 500 may then be repeated as necessary in step 600 on the third portion of the rock sample, the fourth portion of the rock sample, and so forth. The additional portions rock samples after being subjecting to the preparation procedure in step 300 may be subjected to the UCS testing in step 400 under the same conditions as the first portion of the rock sample and the second portion of the rock sample but using a different water-based mud or water-based mud analog. The UCS testing of the rock samples may yield a second UCS value ($UCS_2$) and a third UCS value ($UCS_3$). These UCS values may be compared using Equation 1 in step 500, except $UCS_2$ and $UCS_3$. may be substituted in the equation for $UCS_1$.

As the shale rock sample from the upper portion of the formation should be provided for testing in as close to a virgin rock state as possible, special care must be exercised in drilling, recovering, and providing the sample to the lab for testing. The process steps that may be used for such recovery process are generally known in the field.

The methods steps for UCS testing using a UCS testing apparatus are similar to those described previously. A portion of the shale rock sample is placed in a test vessel. The portion placed in the test apparatus may be the first portion that has not been physio-mechanically altered with one or more water-based drilling muds, or it may be one of the samples which has been physio-mechanically altered with one or more water-based drilling muds. The sample may be subjected to a linear force using the UCS testing apparatus, where the force is continuously increased until the shale rock sample fails. Once the sample fails, the UCS testing apparatus may display the force at time of failure. This is the UCS value obtained by the test.

Figure 2:
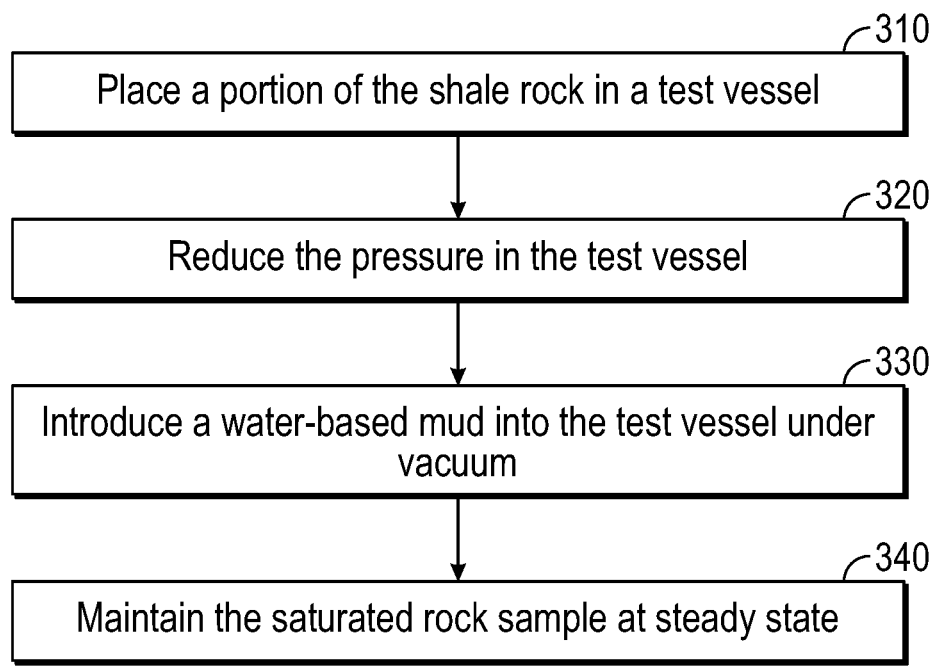
FIG. 2 is a simplified block flow diagram of a testing procedure according to one or more embodiments disclosed.

The preparation procedure for the shale rock samples is illustrated in FIG. 2. The second portion, third portion, and fourth portion of the shale rock sample may be placed in a test vessel in step 310. The test vessel may be equipped with one or more vacuum pumps that may reducing the pressure inside the vessel to a sub-atmospheric pressure. In some embodiments, an absolute or near absolute vacuum may be achieved. In some embodiments, the test vessel may have an internal pressure of between 1 pascal (Pa) and 100,000 Pa.

After the test vessel has been placed under vacuum in step 320, a water-based mud or water-based mud analog may be introduced into the test vessel in step 330. In step 340, the sample is maintained in a steady state condition in the test vessel for a period in a range of from about 4 to 20 hours such that the water-based mud or water-based mud analog permeates the rock sample, producing a saturated sample containing the water-based mud or water-based mud analog. This process prepares the second portion of the rock sample, the third portion of the rock sample, and the fourth portion of the rock sample for UCS testing under degraded conditions which may be similar to those found in wellbore rocks after drilling operations have been performed.

EXAMPLE

Fluid sensitivity of several water-based muds were evaluated using the method described previously and the FSI determined.

Four shale samples were prepared from the same core of a shale rock. These shale samples were taken from the same section of the core that has similar mineralogical composition and physical characteristics. Three core samples were selected for preparation using inhibitive mud systems to evaluate the respective FSI values. A vacuum pump was used for quick saturation and interaction with mud systems to simulate the wellbore environment.

Figure 3:
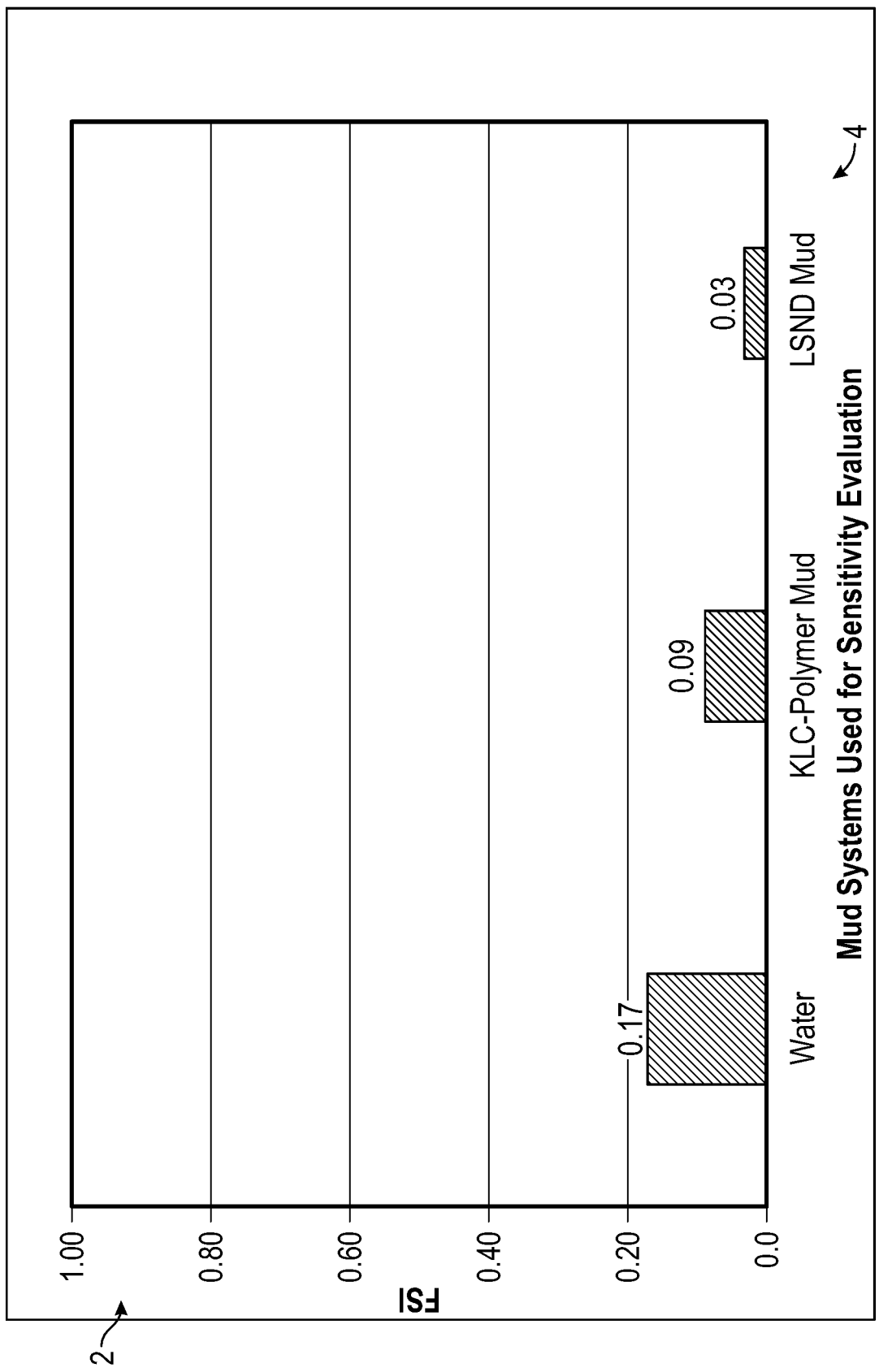
FIG. 3 is a graph illustrating the results of a testing procedure according to one or more embodiments disclosed.

One rock sample was tested without any interaction with a water-based mud as the control sample. Water was selected to represent the most aggressive water-based mud analog. After saturation for 16 hours, the UCS of virgin, uninteracted rock, water interacted rock, a KCl-Polymer mud interacted rock, and a low solids non-dispersed (LSND) drilling mud interacted rock sample were determined using the UCS testing apparatus. Based on the measured UCS values, the FSI for water, KCl-polymer, and LSND mud were calculated using Equation (1). FIG. 3 illustrates the resulting FSI values. In FIG. 3, y-axis 2 indicates the FSI value. The FSI value of water 6, FSI value of KCl-polymer mud 8, and FSI value of LSND mud are indicated on x-axis 4.

The experimental data shows the greatest FSI value for water that represent a highly reactive water-based mud with an FSI of 0.17. The inhibitive KCl-polymer drilling mud shows the second greatest FSI value with an FSI of 0.09. The LSND drilling mud indicates the lowest FSI value with an FSI of 0.03. Accordingly, the method and FSI parameter clearly demonstrate the physio-mechanical aspect of rock-fluid interactions.

Due to the high FSI value of water-based muds, the method disclosed may provide for comprehensive, reliable, and repeatable testing method for determining which inhibitive water-based muds are best suited for a particular shale rock environment.

Unless defined otherwise, all technical and scientific terms used have the same meaning as commonly understood by one of ordinary skill in the art to which these systems, apparatuses, methods, processes, and compositions belong.

The singular forms "a," "an," and "the" include plural referents, unless the context clearly dictates otherwise.

As used here and in the appended claims, the words "comprise," "has," and "include" and all grammatical variations thereof are each intended to have an open, non-limiting meaning that does not exclude additional elements or steps.

"Optionally" means that the subsequently described event or circumstances may or may not occur. The description includes instances where the event or circumstance occurs and instances where it does not occur.

When the word "approximately" or "about" are used, this term may mean that there can be a variance in value of up to ±10%, of up to 5%, of up to 2%, of up to 1%, of up to 0.5%, of up to 0.1%, or up to 0.01%.

Ranges may be expressed as from about one particular value to about another particular value, inclusive. When such a range is expressed, it is to be understood that another embodiment is from the one particular value to the other particular value, along with all particular values and combinations thereof within the range.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, any means-plus-function clauses are intended to cover the structures described herein as performing the recited function(s) and equivalents of those structures. Similarly, any step-plus-function clauses in the claims are intended to cover the acts described here as performing the recited function(s) and equivalents of those acts. It is the express intention of the applicant not to invoke 35 U.S.C. § 112(f) for any limitations of any of the claims herein, except for those in which the claim expressly uses the words "means for" or "step for" together with an associated function.

What is claimed:

1. A method of evaluating fluid sensitivity of a water-based muds on a shale rock, the method comprising:
   providing a sample of the shale rock from a portion of a formation, where the portion of the formation is positioned outside of a reservoir region;
   separating the sample of the shale rock into a first portion and a second portion;
   detecting a first uniaxial compressive strength (UCS) value ($UCS_o$) by subjecting the first portion to a UCS test;
   converting the second portion into a prepared sample utilizing a test preparation procedure;
   detecting a second UCS value ($UCS_1$) by subjecting the prepared sample to the UCS test; and
   determining a fluid sensitivity index (FSI) value utilizing the detected $UCS_0$ and $USC_1$ values.

2. The method of claim 1, where the uniaxial compressive strength (USC) test comprises:
   placing a portion of the sample of the shale rock into a UCS testing apparatus;
   applying a linear force using the UCS testing apparatus to the portion of the sample of the shale rock until the portion of the sample of the shale rock fails; and
   detecting a value for the linear force at the moment of failure.

3. The method of claim 1, where the test preparation procedure comprises:
   introducing the second portion in a test vessel;
   reducing the pressure inside the vessel to a sub-atmospheric condition;
   introducing the water-based mud into the test vessel under vacuum; and
   maintaining the second portion at a steady state condition in the test vessel for a period in a range of from about 4 to 20 hours to produce a saturated sample.

4. The method of claim 1, where the separating the sample of the shale rock further comprises separating the sample of the shale rock into a third portion and a fourth portion.

5. The method of claim 4, further comprising subjecting the first portion to the uniaxial compressive strength test.

6. The method of claim 4, further comprising converting the second portion into a prepared sample utilizing a test preparation procedure and feeding a water stream to the test vessel as the water-based mud.

7. The method of claim 4, further comprising converting the third portion into a prepared sample utilizing a test preparation procedure and feeding a KCl-polymer based mud to the test vessel as the water-based mud.

8. The method of claim 4, further comprising converting the fourth portion into a prepared sample utilizing a test preparation procedure and feeding an LSND-mud (low solids non-dispersed mud) to the test vessel as the water-based mud.

* * * * *